United States Patent

Miyaki

(10) Patent No.: US 9,028,414 B2
(45) Date of Patent: May 12, 2015

(54) ULTRASONIC OBSERVATION APPARATUS, OPERATION METHOD OF THE SAME, AND COMPUTER READABLE RECORDING MEDIUM

(75) Inventor: Hironaka Miyaki, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 141 days.

(21) Appl. No.: 13/561,443

(22) Filed: Jul. 30, 2012

(65) Prior Publication Data

US 2013/0030296 A1    Jan. 31, 2013

Related U.S. Application Data

(63) Continuation of application No. PCT/JP2011/076027, filed on Nov. 11, 2011.

(30) Foreign Application Priority Data

Nov. 11, 2010    (JP) .................... 2010-253290

(51) Int. Cl.
*A61B 8/08*    (2006.01)
*G01S 7/52*    (2006.01)

(52) U.S. Cl.
CPC ......... *G01S 7/52098* (2013.01); *G01S 7/52033* (2013.01); *G01S 7/52036* (2013.01);
(Continued)

(58) Field of Classification Search
CPC ............ G01S 7/52033; G01S 7/52098; G01S 7/52036
USPC ....................................................... 600/442
See application file for complete search history.

(56) References Cited

U.S. PATENT DOCUMENTS

| 4,016,750 A | 4/1977 | Green |
| 4,092,867 A * | 6/1978 | Matzuk .......................... 73/609 |

(Continued)

FOREIGN PATENT DOCUMENTS

| JP | 60-116338 A | 6/1985 |
| JP | 62-167542 A | 7/1987 |

(Continued)

OTHER PUBLICATIONS

Notice of Rejection dated Oct. 16, 2012 from corresponding Japanese Patent Application No. 2012-533410, together with an English language translation.

(Continued)

*Primary Examiner* — Unsu Jung
*Assistant Examiner* — Daniel Huntley
(74) *Attorney, Agent, or Firm* — Scully, Scott, Murphy & Presser, P.C.

(57) ABSTRACT

An ultrasonic observation apparatus is provided with a signal amplifier which amplifies a signal of an ultrasonic wave received from a sample with an amplification factor according to a receiving depth in order to use the signal in generating a B-mode image, a B-mode image data generator which generates B-mode image data in which the amplitude of the signal of the ultrasonic wave amplified by the signal amplifier is converted into brightness for display, an amplification corrector which performs correction to cancel the influence of the amplification by the signal amplifier in order to make the amplification factor constant with respect to the signal of the ultrasonic wave amplified by the signal amplifier regardless of the receiving depth, a frequency analyzer which calculates a frequency spectrum by analyzing the frequency of the signal of the ultrasonic wave corrected by the amplification corrector, and a feature data extractor which extracts feature data of the sample by performing an approximation process and an attenuation correction process for reducing the contribution of the attenuation occurring in accordance with the receiving depth of the ultrasonic wave and the frequency in transmitting the ultrasonic wave.

11 Claims, 11 Drawing Sheets

(52) U.S. Cl.
CPC . *A61B 8/08* (2013.01); *A61B 8/485* (2013.01); *A61B 8/5207* (2013.01); *A61B 8/5223* (2013.01); *A61B 8/5292* (2013.01)

(56) References Cited

U.S. PATENT DOCUMENTS

| | | | |
|---|---|---|---|
| 4,594,896 | A | 6/1986 | Cardoso et al. |
| 2004/0215075 | A1 | 10/2004 | Zagzebski et al. |
| 2004/0243001 | A1 | 12/2004 | Zagzebski et al. |
| 2005/0165309 | A1 | 7/2005 | Varghese et al. |
| 2006/0064014 | A1 | 3/2006 | Falco et al. |
| 2008/0051659 | A1 | 2/2008 | Waki et al. |
| 2010/0099989 | A1 | 4/2010 | Falco et al. |
| 2010/0130860 | A1* | 5/2010 | Yamagata .................... 600/443 |

FOREIGN PATENT DOCUMENTS

| | | |
|---|---|---|
| JP | 10-216143 A | 8/1998 |
| JP | 2004-310639 A | 11/2004 |
| JP | 2005-110833 A | 4/2005 |
| JP | 2006-524115 A | 10/2006 |
| JP | 2009-82624 A | 4/2009 |
| WO | WO 2004/093671 A2 | 11/2004 |
| WO | WO 2005/122906 A1 | 12/2005 |

OTHER PUBLICATIONS

International Search Report PCT/JP2011/076027 dated Feb. 14, 2012.

Saito, Y., et al. "Measurement of Ultrasonic Backscattering Property Caused by Change in the Scatterer's Radius for Assessment of Red Blood Cell Aggregation", Technical Report of IEICE, US2008-36, 2008.09, pp. 25-28, together with an English language abstract.

Sareen, M., et al. "Normalization and Backscatter Spectral Analysis of Human Carotid Arterial Data Acquired using a Clinical Linear Array Ultrasound Imaging System", Conf. Proc.IEEE, Eng.Med. Biol.Soc. 2008, pp. 2968-2971.

Katouzian, A. et al. "Challenges in Artherosclerotic Plaque Characterization with Intravascular Ultrasound (IVUS): From Data Collection to Classification", IEEE Trans. Inf. Technol. Biomed., May 2008, 12(3), pp. 315-327.

* cited by examiner

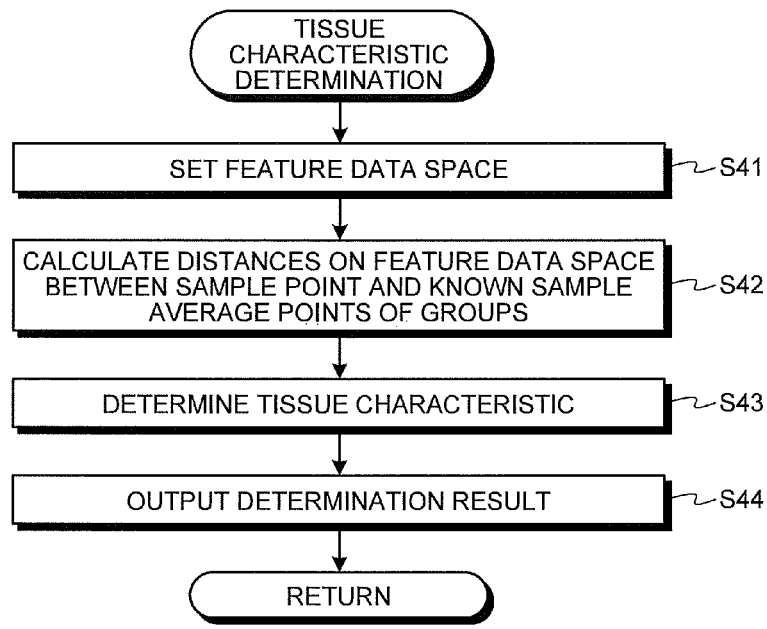
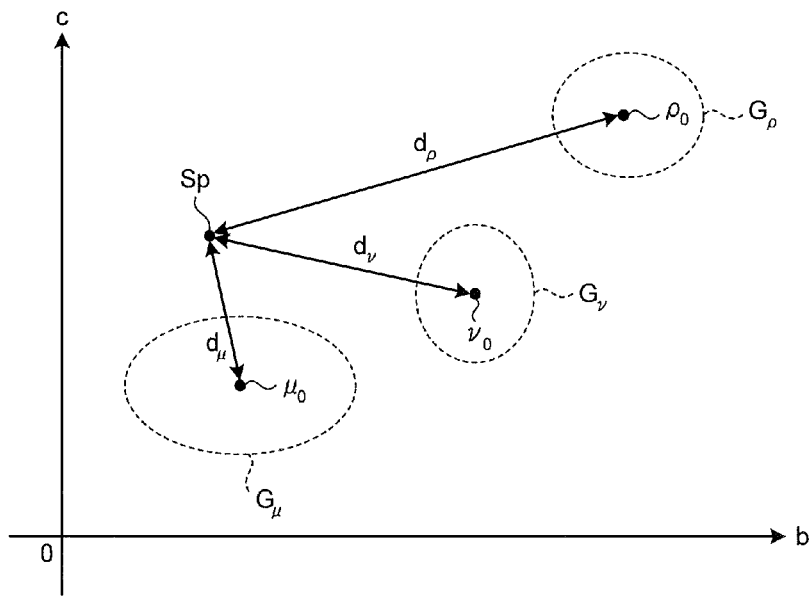

ULTRASONIC OBSERVATION APPARATUS, OPERATION METHOD OF THE SAME, AND COMPUTER READABLE RECORDING MEDIUM

CROSS REFERENCES TO RELATED APPLICATIONS

This application is a continuation of PCT international application Ser. No. PCT/JP2011/76027 filed on Nov. 11, 2011 which designates the United States, incorporated herein by reference, and which claims the benefit of priority from Japanese Patent Application No. 2010-253290, filed on Nov. 11, 2010, incorporated herein by reference.

BACKGROUND OF THE INVENTION

1. Field of the Invention

The present invention relates to an ultrasonic observation apparatus which observes the tissue of a sample using ultrasonic waves, an operation method of the ultrasonic observation apparatus, and a computer readable recording medium.

2. Description of the Related Art

Hitherto, an ultrasonic elastography technique has been known as a technique for examining breast cancer or the like using ultrasonic waves (for example, see WO 2005/122906). Ultrasonic elastography is a technique using the fact that the hardness of cancer or tumor tissue in vivo varies depending on the progress of a disease or a living body. In this technique, in a state in which an examination site is pressed from the outside, the distortion amount or elastic modulus of a living tissue in the examination site is measured using ultrasonic waves, and the result of the measurement is displayed as a tomographic image.

In the observation using ultrasonic waves, attenuation caused by the transmission of an ultrasonic wave is corrected to perform A/D conversion in an optimum range, and thus Sensitivity Time Control (STC) correction is usually performed on received data (analog signal) for generating a B-mode image to add a higher amplification factor to the received data at a deep position (for example, see Japanese Laid-open Patent Publication No. 10-216143).

SUMMARY OF THE INVENTION

An ultrasonic observation apparatus according to the present invention sends an ultrasonic wave to a sample and receives the ultrasonic wave reflected by the sample, the apparatus including: a signal amplifier which amplifies a signal of the ultrasonic wave received from the sample with an amplification factor according to a receiving depth in order to use the signal in generating a B-mode image; a B-mode image data generator which generates B-mode image data in which the amplitude of the signal of the ultrasonic wave amplified by the signal amplifier is converted into brightness and displayed; an amplification corrector which performs correction to cancel the influence of the amplification by the signal amplifier in order to make the amplification factor constant with respect to the signal of the ultrasonic wave amplified by the signal amplifier regardless of the receiving depth; a frequency analyzer which calculates a frequency spectrum by analyzing the frequency of the signal of the ultrasonic wave corrected by the amplification corrector; and a feature data extractor which extracts feature data of the sample by performing an approximation process and an attenuation correction process for reducing the contribution of the attenuation occurring in accordance with the receiving depth of the ultrasonic wave and the frequency in transmitting the ultrasonic wave.

A method of operating an ultrasonic observation apparatus according to the present invention sends an ultrasonic wave to a sample and receives the ultrasonic wave reflected by the sample, the method including: amplifying a signal of the ultrasonic wave received from the sample with an amplification factor according to a receiving depth in order to use the signal in generating a B-mode image; generating B-mode image data in which the amplitude of the amplified signal of the ultrasonic wave is converted into brightness for display using a B-mode image data generator; performing correction to cancel the influence of the amplification in order to make the amplification factor constant with respect to the amplified signal of the ultrasonic wave regardless of the receiving depth; calculating a frequency spectrum using a frequency analyzer by analyzing the frequency of the corrected signal of the ultrasonic wave; and extracting feature data of the sample using a feature data extractor by performing an approximation process and an attenuation correction process for reducing the contribution of the attenuation occurring in accordance with the receiving depth of the ultrasonic wave and the frequency in transmitting the ultrasonic wave.

A non-transitory computer readable recording medium on which an executable program is recorded, the program instructing a processor to execute: amplifying a signal of the ultrasonic wave received from the sample with an amplification factor according to a receiving depth in order to use the signal in generating a B-mode image; generating B-mode image data in which the amplitude of the amplified signal of the ultrasonic wave is converted into brightness for display using a B-mode image data generator; performing correction to cancel the influence of the amplification in order to make the amplification factor constant with respect to the amplified signal of the ultrasonic wave regardless of the receiving depth; and calculating a frequency spectrum using a frequency analyzer by analyzing the frequency of the corrected signal of the ultrasonic wave, and extracting feature data of the sample using a feature data extractor by performing an approximation process and an attenuation correction process for reducing the contribution of the attenuation occurring in accordance with the receiving depth of the ultrasonic wave and the frequency in transmitting the ultrasonic wave.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 11 is a flowchart illustrating the outline of a process which is performed by a tissue characteristic determination unit of the ultrasonic observation apparatus according to the first embodiment of the invention;

FIG. 12 is a diagram illustrating an example of a feature data space which is set by the tissue characteristic determination unit of the ultrasonic observation apparatus according to the first embodiment of the invention;

DETAILED DESCRIPTION OF THE PREFERRED EMBODIMENTS

Hereinafter, modes (hereinafter, referred to as "embodiments") for carrying out the invention will be described with reference to the accompanying drawings.

First Embodiment

Figure 1:
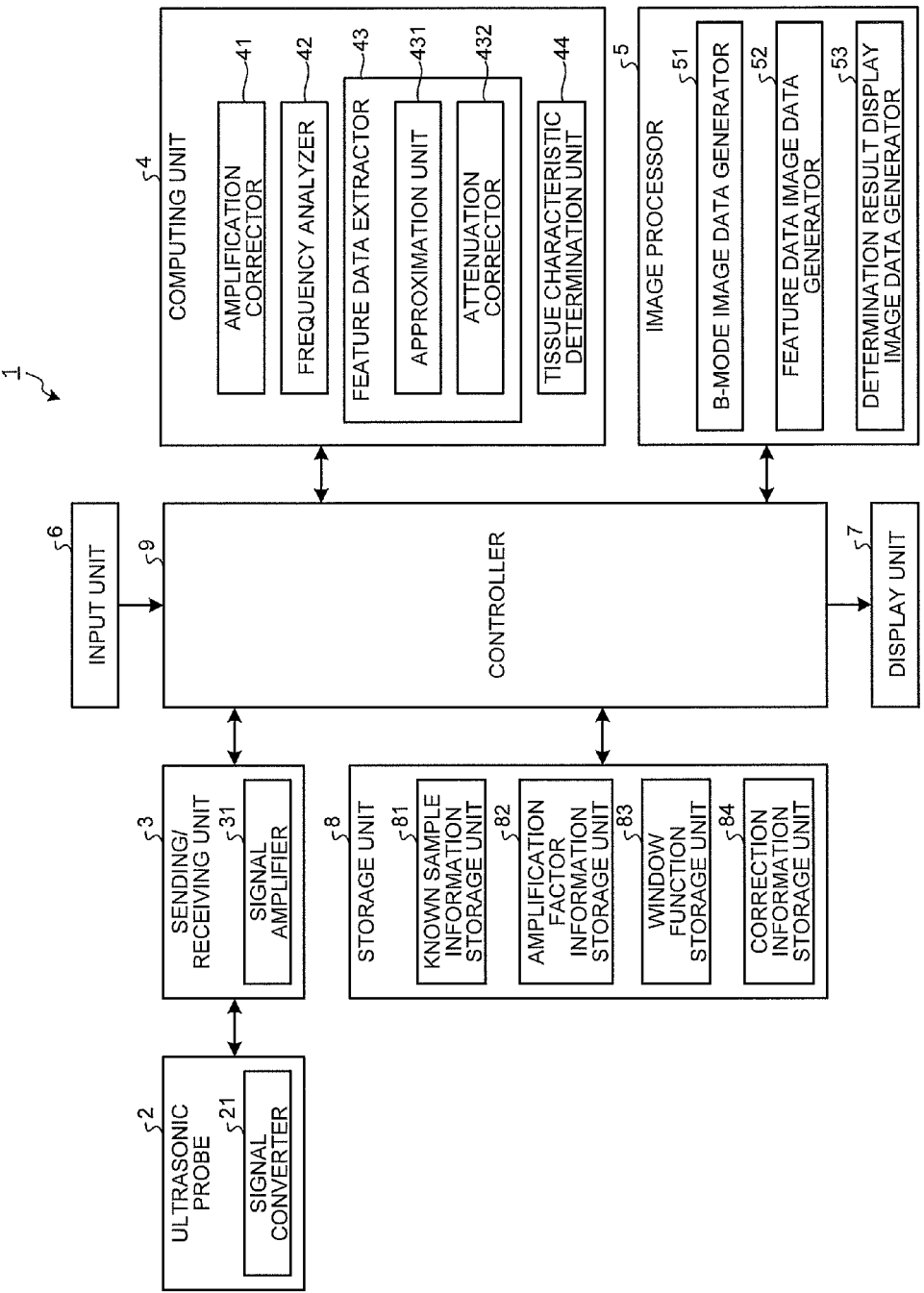
FIG. 1 is a block diagram illustrating the configuration of an ultrasonic observation apparatus according to a first embodiment of the invention.

FIG. 1 is a block diagram illustrating the configuration of an ultrasonic observation apparatus according to a first embodiment of the invention. The ultrasonic observation apparatus 1 illustrated in FIG. 1 is an apparatus which observes a sample using ultrasonic waves.

The ultrasonic observation apparatus 1 is provided with an ultrasonic probe 2 which outputs an ultrasonic pulse to the outside and receives an externally-reflected ultrasonic echo, a sending/receiving unit 3 which sends and receives an electric signal to and from the ultrasonic probe 2, a computing unit 4 which subjects an electric echo signal obtained by converting an ultrasonic echo to predetermined computing, an image processor 5 which generates image data corresponding to an electric echo signal obtained by converting an ultrasonic echo, an input unit 6 which is realized using an interface such as a keyboard, a mouse, and a touch panel and receives input of various information, a display unit 7 which is realized using a display panel formed of liquid crystal, organic EL, or the like and displays various information including an image generated by the image processor 5, a storage unit 8 which stores various information including information related to the tissue characteristics of known samples, and a controller 9 which controls the operation of the ultrasonic observation apparatus 1.

The ultrasonic probe 2 has a signal converter 21 which converts an electric pulse signal received from the sending/receiving unit 3 into an ultrasonic pulse (acoustic pulse signal) and converts an ultrasonic echo reflected from an exterior sample into an electric echo signal. The ultrasonic probe 2 may mechanically scan an ultrasonic transducer, or may electronically scan a plurality of ultrasonic transducers.

The sending/receiving unit 3 is electrically connected to the ultrasonic probe 2 to send a pulse signal to the ultrasonic probe 2 and to receive an echo signal as a received signal from the ultrasonic probe 2. Specifically, the sending/receiving unit 3 generates a pulse signal on the basis of a waveform and sending timing which are set in advance, and sends the generated pulse signal to the ultrasonic probe 2.

Figure 2:
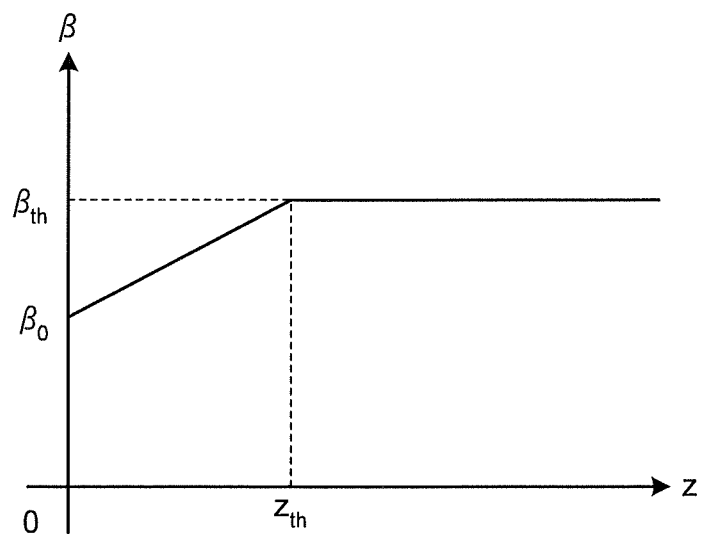
FIG. 2 is a diagram illustrating the relationship between a receiving depth and an amplification factor in an amplification process which is performed by a signal amplifier of the ultrasonic observation apparatus according to the first embodiment of the invention.

The sending/receiving unit 3 has a signal amplifier 31 which amplifies an echo signal. Specifically, the signal amplifier 31 performs STC correction so that the higher the receiving depth of an echo signal, the higher the amplification factor the signal is amplified with. FIG. 2 is a diagram illustrating the relationship between a receiving depth of an echo signal and an amplification factor. A receiving depth z shown in FIG. 2 is an amount which is calculated on the basis of an elapsed time from a time point at which reception of an ultrasonic wave is started. As shown in FIG. 2, an amplification factor $\beta$ linearly increases from $\beta_0$ to $\beta_{th}$ ($>\beta_0$) with an increase of the receiving depth z when the receiving depth z is less than a threshold $z_{th}$. In addition, the amplification factor $\beta$ takes a certain value $\beta_{th}$ when the receiving depth z is equal to or greater than the threshold $z_{th}$. The value of the threshold $z_{th}$ is a value at which the ultrasonic signal received from a sample is almost attenuated and noise is thus dominant. More generally, the amplification factor $\beta$ may monotonically increase with an increase of the receiving depth z when the receiving depth z is less than the threshold $z_{th}$.

The sending/receiving unit 3 subjects the echo signal amplified by the signal amplifier 31 to a process such as filtering, and then A/D converts the processed signal to generate and output a digital RF signal. In the case where the ultrasonic probe 2 electronically scans a plurality of ultrasonic transducers, the sending/receiving unit 3 has a multi-channel circuit for beam synthesis corresponding to the plurality of ultrasonic transducers.

The computing unit 4 has an amplification corrector 41 which performs amplification correction to make the amplification factor constant with respect to the digital RF signal output from the sending/receiving unit 3 regardless of the receiving depth, a frequency analyzer 42 which subjects the digital RF signal subjected to the amplification correction to fast Fourier transform (FFT) to analyze the frequency, a feature data extractor 43 which subjects the frequency spectrum (power spectrum) calculated by the frequency analyzer 42 to an approximation process and a correction process for reducing the contribution of the attenuation of the ultrasonic wave depending on the receiving depth and the frequency of the ultrasonic wave to extract the feature data of the frequency spectrum, and a tissue characteristic determination unit 44 which determines the tissue characteristic of a predetermined area of a sample by using the feature data extracted by the feature data extractor 43.

Figure 3:
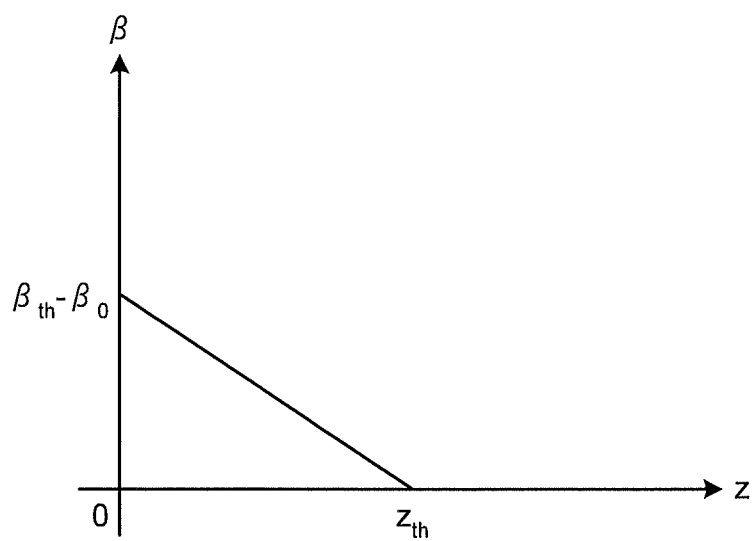
FIG. 3 is a diagram illustrating the relationship between a receiving depth and an amplification factor in an amplification process which is performed by an amplification corrector of the ultrasonic observation apparatus according to the first embodiment of the invention.

FIG. 3 is a diagram illustrating the relationship between a receiving depth and an amplification factor in the amplification process which is performed by the amplification corrector 41. As shown in FIG. 3, the amplification factor of the amplification process which is performed by the amplification corrector 41 is a maximum value $\beta_{th}$-$\beta_0$ at a receiving depth of zero, is linearly reduced at a receiving depth of up to a receiving depth $z_{th}$, and is zero at the receiving depth $z_{th}$ or greater. When a digital RF signal is amplified with such an amplification factor, the influence of the STC correction in the signal amplifier 31 can be offset, and a signal of the certain amplification factor $\beta_{th}$ can be output. Of course, the relationship between the receiving depth z and the amplification factor $\beta$ achieved in the amplification corrector 41 varies in accordance with the relationship between the receiving depth and the amplification factor in the signal amplifier 31.

For each acoustic ray (line data), the frequency analyzer 42 subjects an FFT data group formed of a predetermined data amount to a fast Fourier transform to calculate a frequency spectrum. The frequency spectrum tends to vary depending on the tissue characteristic of a sample. The reason for this is that the frequency spectrum is correlated with the size, density, acoustic impedance, and the like of a sample as a scatterer which scatters an ultrasonic wave.

The feature data extractor 43 has an approximation unit 431 which approximates the frequency spectrum calculated by the frequency analyzer 42 to calculate pre-correction feature data before performing an attenuation correction process, and an attenuation corrector 432 which subjects the pre-correction feature data approximated by the approximation unit 431 to an attenuation correction process to extract the feature data.

The approximation unit 431 approximates the frequency spectrum with a linear expression through regression analysis to extract pre-correction feature data characterizing the linear expression. Specifically, the approximation unit 431 calculates a gradient $a_0$ and an intercept $b_0$ of the linear expression through regression analysis, and calculates, as pre-correction feature data, a strength at a specific frequency in the frequency band in the frequency spectrum. In the first embodiment, although the approximation unit 431 calculates a strength (Mid-band fit) $c_0 = a_0 f_{MID} + b_0$ at a center frequency $f_{MID} = (f_{LOW} + f_{HIGH})/2$, this is just an example. Here, the "strength" is any of parameters such as voltage, electric power, sound pressure, acoustic energy, and the like.

It is thought that among the three pieces of feature data, the gradient $a_0$ is correlated with the size of an ultrasonic scatterer, and generally, the greater the size of the scatterer, the less the value of the gradient. In addition, the intercept $b_0$ is correlated with the size of a scatterer, the difference in the acoustic impedance, the density (concentration) of a scatterer, and the like. Specifically, it is thought that the greater the size of the scatterer, the greater the value of the intercept $b_0$, the greater the size of the acoustic impedance, the greater the value of the intercept $b_0$, and the greater the density (concentration) of the scatterer, the greater the value of the intercept $b_0$. The strength $c_0$ at the center frequency $f_{MID}$ (hereinafter, simply referred to as "strength") is an indirect parameter derived from the gradient $a_0$ and the intercept $b_0$, and gives a spectrum strength at the center in an effective frequency band. Therefore, it is thought that the strength $c_0$ is correlated to some degree with the brightness of a B-mode image in addition to the size of a scatterer, the difference in the acoustic impedance, and the density of a scatterer. The approximate polynomial which is calculated by the feature data extractor 43 is not limited to the linear expression, and a quadratic or higher-order approximate polynomial can also be used.

The correction which is performed by the attenuation corrector 432 will be described. An ultrasonic attenuation amount A can be represented as follows:

$$A = 2\alpha z f \quad (1)$$

Here, $\alpha$ is an attenuation rate, z is the receiving depth of an ultrasonic wave, and f is a frequency. As is obvious from Expression (1), the attenuation amount A is proportional to the frequency f. The specific value of the attenuation rate $\alpha$ is, in the case of a living body, in the range of 0 to 1.0 (dB/cm/MHz), and preferably 0.3 to 0.7 (dB/cm/MHz), and it is determined in accordance with the type of an observation target organ. For example, when the observation target organ is a pancreas, $\alpha = 0.6$ (dB/cm/MHz) is determined. In the first embodiment, a configuration can also be employed in which the value of the attenuation rate $\alpha$ can be changed by an input from the input unit 6.

The attenuation corrector 432 corrects the pre-correction feature data (gradient $a_0$, intercept $b_0$, strength $C_0$) extracted by the approximation unit 431 as follows.

$$a = a_0 + 2\alpha z \quad (2)$$

$$b = b_0 \quad (3)$$

$$c = c_0 + 2\alpha z f_{MID} (= a f_{MID} + b) \quad (4)$$

As is obvious from Expressions (2) and (4), the greater the receiving depth z of the ultrasonic wave, the greater the correction amount the attenuation corrector 432 performs correction with. In addition, according to Expression (3), the correction related to the intercept is an identical transformation. The reason for this is that the intercept is a frequency component corresponding to 0 frequency (Hz) and is not subjected to attenuation.

The tissue characteristic determination unit 44 calculates, for each feature data, an average and a standard deviation of the feature data of the frequency spectrum extracted by the feature data extractor 43 and corrected by the attenuation corrector 432. The tissue characteristic determination unit 44 determines the tissue characteristic of a predetermined area of a sample by using the calculated average and standard deviation and by using averages and standard deviations of the feature data of frequency spectrums of known samples which are stored in the storage unit 8. Here, the "predetermined area" is an area in an image which is designated by an operator of the ultrasonic observation apparatus 1, who has seen the image generated by the image processor 5, using the input unit 6 (hereinafter, referred to as "area of interest"). In addition, the "tissue characteristic" is any of cancer, endocrine tumor, mucinous tumor, normal tissue, normal blood vessel, and the like. When the sample is a pancreas, chronic pancreatitis, autoimmune pancreatitis, and the like are also included as tissue characteristics.

The average and the standard deviation of the feature data which are calculated by the tissue characteristic determination unit 44 reflect a change at a cell level such as enlargement of a nucleus and variants and a change in the tissue such as hyperplasia of fibers and substitution with fibers of a parenchymal tissue in an interstitium, and shows unique values in accordance with the tissue characteristic. Accordingly, the tissue characteristic of a predetermined area of a sample can be accurately determined by using the average and the standard deviation of the feature data.

The image processor 5 has a B-mode image data generator 51 which generates B-mode image data from an echo signal, a feature data image data generator 52 which generates feature data image data to display visual information corresponding to the feature data of a sample, and a determination result display image data generator 53 which generates determination result display image data to display a determination result of the tissue characteristic of the area of interest and information related to the determination result by using the data output by the B-mode image data generator 51 and the computing unit 4.

The B-mode image data generator 51 subjects a digital signal to a signal process using a known technique such as a band-pass filter, logarithmic transformation, gain processing, or contrast processing, and performs data culling according to a data step width determined in accordance with the display range of an image in the display unit 7 to generate B-mode image data.

The visual information to be used in generating the feature data image data by the feature data image data generator 52 is a variable constituting a color space such as a RGB color system having R (red), G (green), and B (blue) as variables.

The determination result display image data generator 53 generates determination result display image data including the B-mode image data generated by the B-mode image data generator 51, the feature data image data generated by the feature data image data generator 52, the feature data extracted by the feature data extractor 43, and the determination result obtained by determination of the tissue characteristic determination unit 44.

The storage unit 8 is provided with a known sample information storage unit 81 which stores information of known samples, an amplification factor information storage unit 82 which stores information of the amplification factor referred to when the signal amplifier 31 and the amplification corrector 41 perform an amplification process, a window function storage unit 83 which stores a window function to be used in the frequency analysis process which is performed by the frequency analyzer 42, and a correction information storage unit 84 which stores correction information referred to when the attenuation corrector 432 performs a process.

The known sample information storage unit 81 stores feature data of the frequency spectrums extracted with respect to known samples in association with the tissue characteristics of the known samples. In addition, the known sample information storage unit 81 stores, with respect to the feature data of the frequency spectrum related to the known samples, an average and a standard deviation calculated for each of the groups classified on the basis of the tissue characteristics of the known samples in addition to all pieces of feature data of the known samples. Here, the feature data of the known samples is extracted in the same manner as in the first embodiment. However, there is no need that the ultrasonic observation apparatus 1 should perform the process of extracting the feature data of the known samples. It is desirable that the information of the known samples stored in the known sample information storage unit 81 has high reliability in terms of the tissue characteristics. The amplification factor information storage unit 82 stores the relationships between the amplification factor and the receiving depth, which are shown in FIGS. 2 and 3. The window function storage unit 83 stores at least one of the window functions such as Hamming, Hanning, and Blackman. The correction information storage unit 84 stores information related to the conversion of Expressions (2) to (4).

The storage unit 8 is realized using a ROM which stores an operating program of the ultrasonic observation apparatus according to the first embodiment, a program for operating a predetermined OS, and the like in advance, a RAM which stores computing parameters and data of the respective processes, or the like.

The constituent elements other than the ultrasonic probe 2 of the ultrasonic observation apparatus 1 having the above-described functions and configurations are realized using a computer provided with a CPU having a computing function and a control function. The CPU of the ultrasonic observation apparatus 1 reads out the information stored in the storage unit 8 and various programs including the above-described operating program of the ultrasonic observation apparatus from the storage unit 8 to execute a computing process related to a method of operating the ultrasonic observation apparatus according to the first embodiment.

The operating program of the ultrasonic observation apparatus according to the first embodiment can also be stored on a computer readable recording medium such as a hard disk, a flash memory, a CD-ROM, a DVD-ROM, or a flexible disk to be widely distributed.

Figure 4:
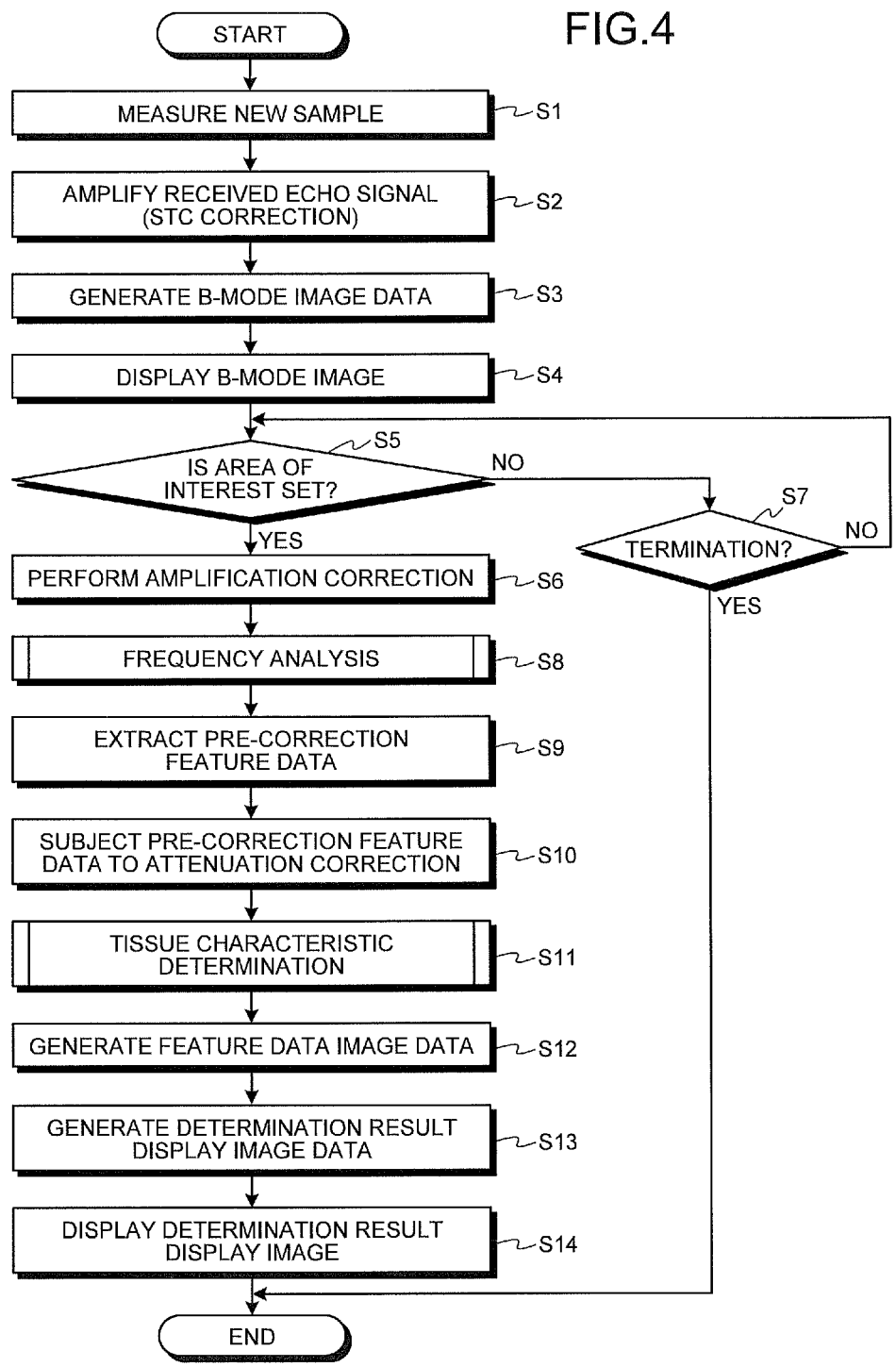
FIG. 4 is a flowchart illustrating the outline of a process of the ultrasonic observation apparatus according to the first embodiment of the invention.

FIG. 4 is a flowchart illustrating the outline of a process of the ultrasonic observation apparatus 1 having the above-described configurations. In FIG. 4, first, the ultrasonic observation apparatus 1 measures a new sample using the ultrasonic probe 2 (Step S1).

Next, the signal amplifier 31 receiving an echo signal from the ultrasonic probe 2 amplifies the echo signal (Step S2). Here, the signal amplifier 31 performs amplification on the basis of the relationship between the amplification factor and the receiving depth shown in FIG. 2.

Then, the B-mode image data generator 51 generates B-mode image data using an echo signal for a B-mode image which is output from the sending/receiving unit 3 (Step S3).

Figure 5:
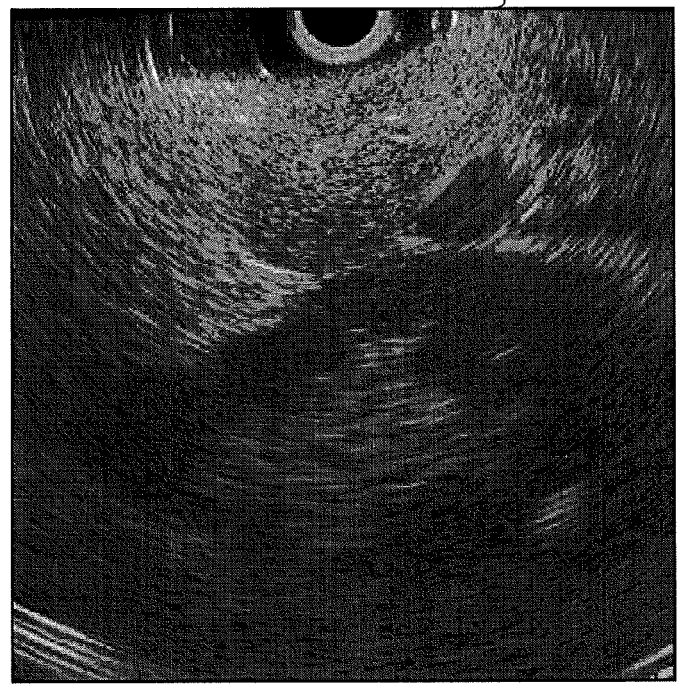
FIG. 5 is a diagram illustrating a display example of a B-mode image in a display unit of the ultrasonic observation apparatus according to the first embodiment of the invention.

Next, the controller 9 controls the display unit 7 to display a B-mode image corresponding to the B-mode image data generated by the B-mode image data generator 51 (Step S4). FIG. 5 is a diagram illustrating a display example of a B-mode image in the display unit 7. A B-mode image 100 shown in FIG. 5 is a gray scale image in which values of R (red), G (green), and B (blue), which are variables when a RGB color system is employed as a color space, are matched.

Then, when an area of interest is set through the input unit 6 (Step S5: Yes), the amplification corrector 41 performs correction to make the amplification factor constant with respect to the signal output from the sending/receiving unit 3 regardless of the receiving depth (Step S6). Here, the amplification corrector 41 performs an amplification process on the basis of the relationship between the amplification factor and the receiving depth shown in FIG. 3.

On the other hand, when no area of interest is set (Step S5: No), the ultrasonic observation apparatus 1 terminates the process when an instruction for terminating the process is input by the input unit 6 (Step S7: Yes). On the contrary, when no area of interest is set (Step S5: No), the ultrasonic observation apparatus 1 returns to Step S5 when an instruction for terminating the process is not input by the input unit 6 (Step S7: No).

After Step S6, the frequency analyzer 42 calculates a frequency spectrum by analyzing the frequency through FFT computing (Step S8). In the Step S8, the entire image area can also be set as an area of interest.

Figure 6:
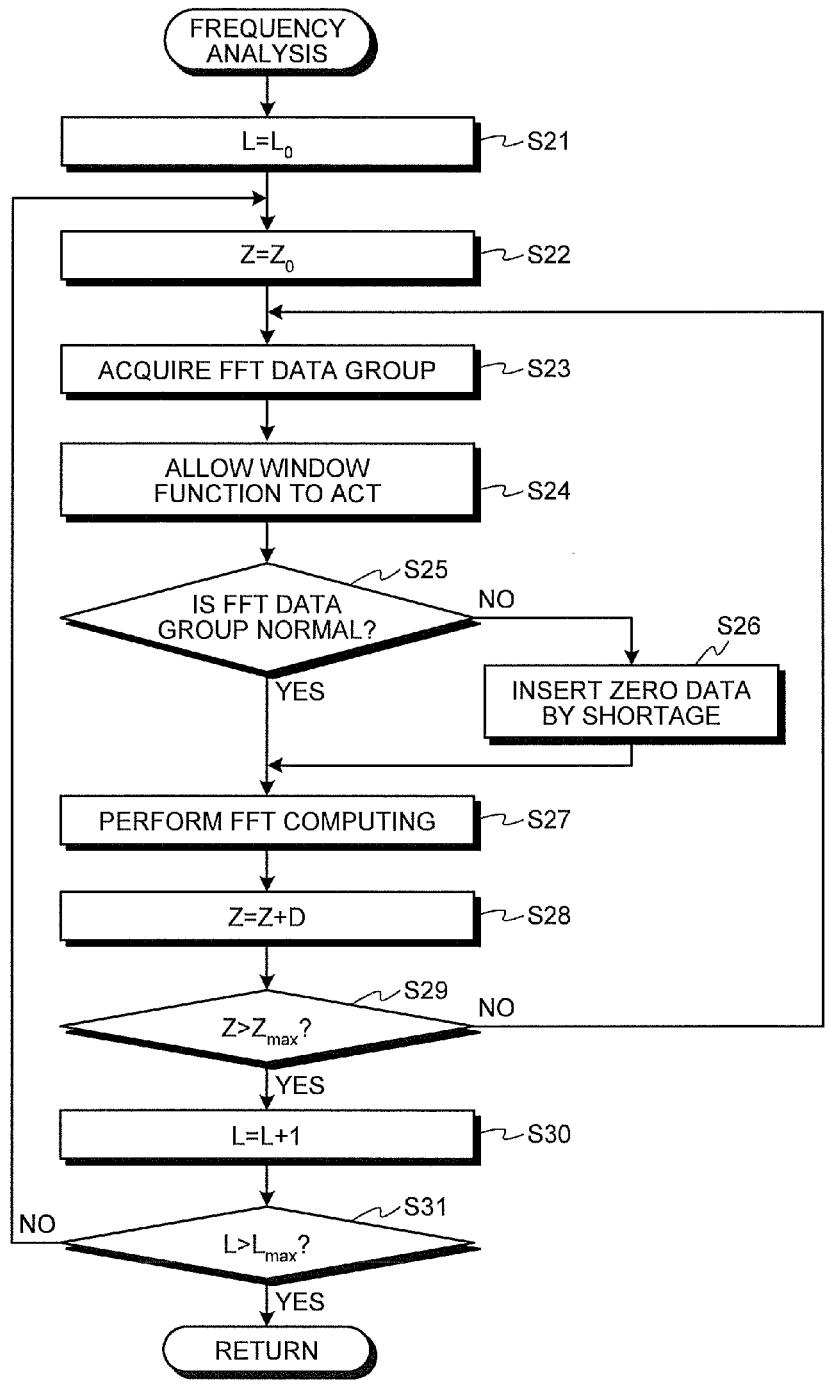
FIG. 6 is a flowchart illustrating the outline of a process which is performed by a frequency analyzer of the ultrasonic observation apparatus according to the first embodiment of the invention.

Here, the process which is performed by the frequency analyzer 42 (Step S8) will be described in detail with reference to the flowchart shown in FIG. 6. First, the frequency analyzer 42 sets an acoustic ray number L of an acoustic ray which is an analysis target as an initial value $L_0$ (Step S21). The initial value $L_0$ may be imparted to, for example, an acoustic ray which is initially received by the sending/receiving unit 3, or an acoustic ray corresponding to a boundary position on one of the right and left sides of the area of interest set by the input unit 6.

Figure 7:
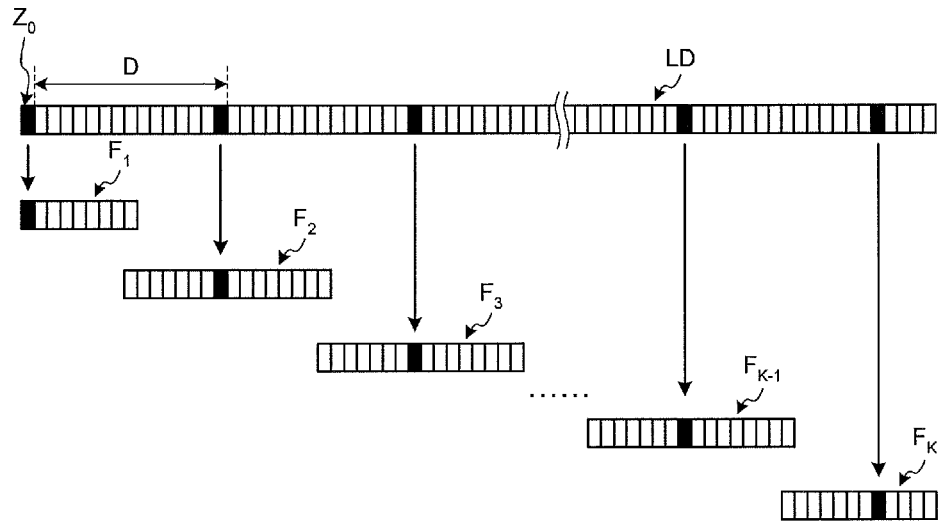
FIG. 7 is a diagram schematically illustrating data arrangement of one acoustic ray.

Next, the frequency analyzer 42 calculates frequency spectrums of all of a plurality of data positions set on one acoustic ray. First, the frequency analyzer 42 sets an initial value $Z_0$ of a data position Z (corresponding to the receiving depth) representing a series of data groups (FFT data groups) acquired for FFT computing (Step S22). FIG. 7 is a diagram schematically illustrating data arrangement of one acoustic ray. In an acoustic ray LD shown in FIG. 7, the white or black rectangle means one data. The acoustic ray LD is made discrete at time intervals corresponding to a sampling frequency (for example, 50 MHz) in A/D conversion which is performed by the sending/receiving unit 3. FIG. 7 shows the case in which the first data of the acoustic ray LD is set as the initial value $Z_0$ of the data position Z. FIG. 7 is a just an example, and the position of the initial value $Z_0$ can be arbitrarily set. For example, a data position Z corresponding to an upper end position of the area of interest may be set as the initial value $Z_0$.

Then, the frequency analyzer 42 acquires an FFT data group at the data position Z (Step S23) and allows a window function stored in the window function storage unit 83 to act on the acquired FFT data group (Step S24). When the window function acts on the FFT data group in this manner, discontinuity of the FFT data groups at the boundary can be avoided, and an artifact can be prevented from occurring.

Next, the frequency analyzer 42 determines whether or not the FFT data group at the data position Z is a normal data group (Step S25). Here, it is necessary for the FFT data group to have the number of pieces of data being a power of two. Hereinafter, the FFT data group has $2^n$ (n is a positive integer) pieces of data. The normal FFT data group means that the data position Z is a $2^{n-1}$-th position from the front in the FFT data group. In other words, the normal FFT data group means that there are $2^{n-1}-1$ (=N) pieces of data before the data position Z, and there are $2^{n-1}$ (=M) pieces of data after the data position Z. In FIG. 7, the FFT data groups $F_2$, $F_3$, and $F_{K-1}$ are normal, and the FFT data groups $F_1$ and $F_K$ are abnormal. In FIG. 7, n=4 is set (N=7, M=8).

As a result of the determination in Step S25, when the FFT data group at the data position Z is normal (Step S25: Yes), the frequency analyzer 42 proceeds to Step S27 to be described later.

As a result of the determination in Step S25, when the FFT data group at the data position Z is not normal (Step S25: No), the frequency analyzer 42 generates a normal FFT data group by inserting zero data by a shortfall (Step S26). For the FFT data group which has been determined to be abnormal in Step S25, a window function acts before the addition of zero data. Therefore, data discontinuity does not occur even when zero data is inserted into the FFT data group. After Step S26, the frequency analyzer 42 proceeds to Step S27 to be described later.

Figure 8:
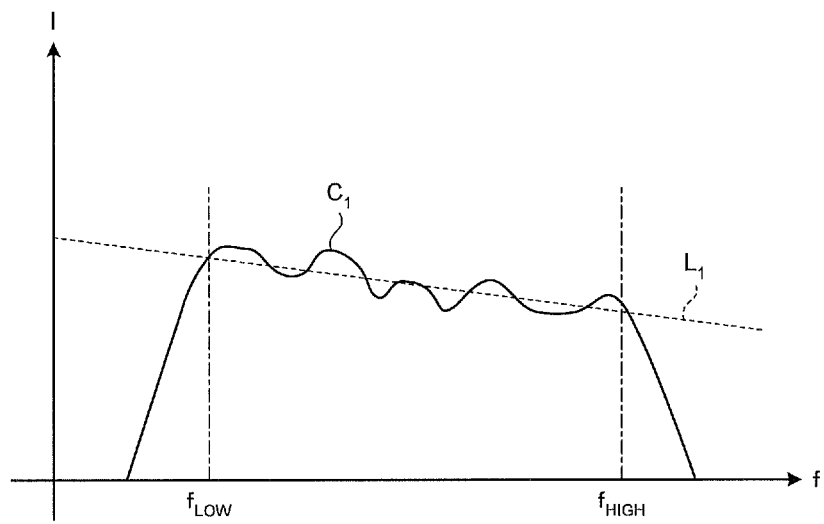
FIG. 8 is a diagram illustrating an example (first example) of a frequency spectrum which is calculated by the frequency analyzer of the ultrasonic observation apparatus according to the first embodiment of the invention.
Figure 9:
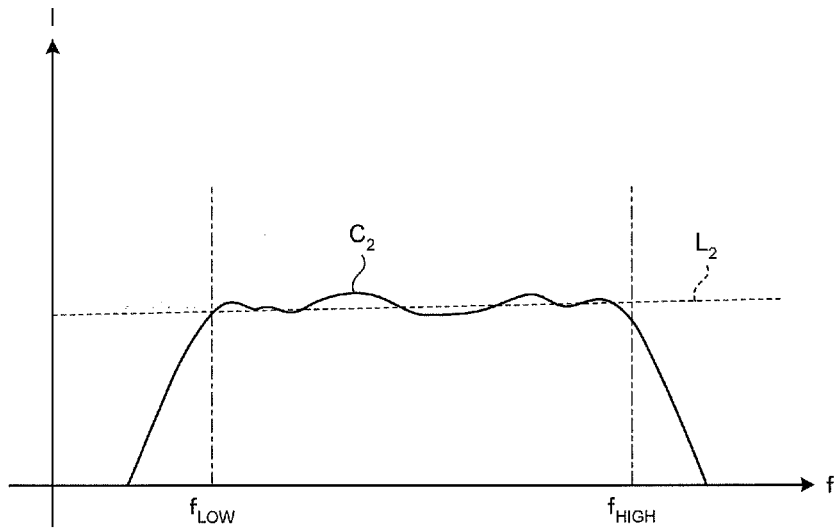
FIG. 9 is a diagram illustrating an example (second example) of a frequency spectrum which is calculated by the frequency analyzer of the ultrasonic observation apparatus according to the first embodiment of the invention.

In Step S27, the frequency analyzer 42 obtains a frequency spectrum by performing FFT computing using the FFT data group (Step S27). FIGS. 8 and 9 are diagrams illustrating an example of the frequency spectrum calculated by the frequency analyzer 42. In FIGS. 8 and 9, a horizontal axis f represents a frequency, and a vertical axis I represents a strength. In frequency spectrum curves $C_1$ and $C_2$ shown in FIGS. 8 and 9, respectively, a minimum frequency $f_{Low}$ and a maximum frequency $f_{HIGH}$ of the frequency spectrum are parameters which are determined on the basis of the frequency band of the ultrasonic probe 2, the frequency band of the pulse signal sent from the sending/receiving unit 3, and the like. For example, $f_{LOW}$=3 MHz, and $f_{HIGH}$=10 MHz. A straight line $L_1$ shown in FIG. 8 and a straight line $L_2$ shown in FIG. 9 will be described in a description about a feature data extraction process. In the first embodiment, the curve and the straight line are formed of a set of discrete points. The same is true of embodiments to be described later.

Next, the frequency analyzer 42 adds a predetermined data step width D to the data position Z to calculate a data position Z of a FFT data group which is a next analysis target (Step S28). Here, it is desirable that the data step width D is made equal to a data step width which is used in generating B-mode image data by the B-mode image data generator 51. However, when the computing amount in the frequency analyzer 42 is to be reduced, the data step width D may be set to be greater than the data step width which is used by the B-mode image data generator 51. FIG. 7 shows the case in which D=15.

Then, the frequency analyzer 42 determines whether or not the data position Z is greater than a final data position $Z_{max}$ (Step S29). Here, the final data position $Z_{max}$ may be a data length of the acoustic ray LD, or may be a data position corresponding to a lower end of the area of interest. As a result of the determination, when the data position Z is greater than the final data position $Z_{max}$ (Step S29: Yes), the frequency analyzer 42 increases an acoustic ray number L by 1 (Step S30). On the other hand, when the data position Z is equal to or less than the final data position $Z_{max}$ (Step S29: No), the frequency analyzer 42 returns to Step S23. In this manner, regarding one acoustic ray LD, the frequency analyzer 42 subjects $[\{(Z_{max}-Z_0)/D\}+1]$ (=K) FFT data groups to FFT computing. Here, [X] represents a maximum integer not exceeding X.

When the acoustic lay number L increased in Step S30 is greater than a final acoustic ray number $L_{max}$ (Step S31: Yes), the frequency analyzer 42 returns to the main routine shown in FIG. 4. On the other hand, when the acoustic lay number L increased in Step S30 is equal to or less than the final acoustic ray number $L_{max}$ (Step S31: No), the frequency analyzer 42 returns to Step S22.

In this manner, the frequency analyzer 42 performs FFT computing K times for each of $(L_{max}-L_0+1)$ acoustic rays. The final acoustic ray number $L_{max}$ may be imparted to, for example, an acoustic ray which is finally received by the sending/receiving unit 3, or an acoustic ray corresponding to a boundary on one of the right and left sides of the area of interest. Hereinafter, the total number $(L_{max}-L_0+1) \times K$ of FFT computing operations performed for all of the acoustic rays by the frequency analyzer 42 is represented by P.

Next to the above-described frequency analysis process in Step S8, the approximation unit 431 subjects the P frequency spectrums calculated by the frequency analyzer 42 to regression analysis as an approximation process to extract pre-correction feature data (Step S9). Specifically, the approximation unit 431 calculates a linear expression for approximating the frequency spectrum of the frequency band $f_{Low} < f < f_{HIGH}$ through regression analysis, and thus extracts a gradient $a_0$, an intercept $b_0$, and a strength $c_0$ characterizing the linear expression as pre-correction feature data. The straight line $L_1$ shown in FIG. 8 and the straight line $L_2$ shown in FIG. 9 are regression lines which are obtained by subjecting the frequency spectrum curves $C_1$ and $C_2$ to a feature data extraction process in Step S9.

Figure 10:
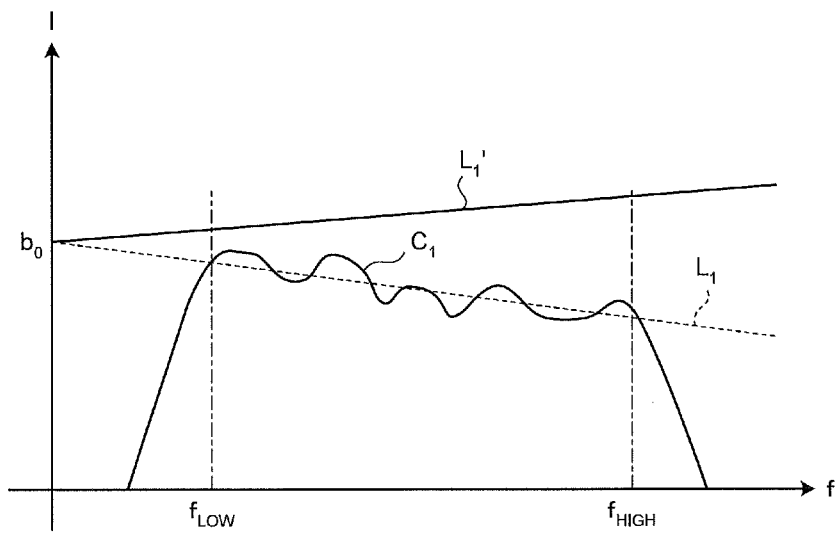
FIG. 10 is a diagram illustrating a new straight line which is determined by feature data after the feature data related to the straight line shown in FIG. 8 is subjected to attenuation correction.

Then, the attenuation corrector 432 subjects the pre-correction feature data extracted by the approximation unit 431 to an attenuation correction process (Step S10). For example, when a sampling frequency of the data is 50 MHz, the time interval of data sampling is 20 (nsec). Here, when the speed of sound is 1,530 (m/sec), the distance interval of data sampling is 1,530 (m/sec)×20 (nsec)/2=0.0153 (mm). When the number of data steps from the first data of the acoustic ray LD to a data position of the FFT data group of the processing target is k, the data position Z is 0.0153 k (mm). The attenuation corrector 432 substitutes the value of the data position Z obtained as above for the receiving depths z of the above-described Expressions (2) to (4) to calculate a gradient a, an intercept b, and a strength c which are feature data of the frequency spectrum. FIG. 10 is a diagram illustrating a straight line which is determined by feature data, related to the straight line $L_1$ shown in FIG. 8, subjected to attenuation correction. The expression representing a straight line $L_1'$ shown in FIG. 10 is as follows:

$$I=af+b=(a_0+2\alpha Z)f+b_0 \quad (5)$$

As is obvious from Expression (5), the straight line $L_1'$ is inclined greater than the straight line $L_1$ and has the same intercept value as that of the straight line $L_1$.

Then, the tissue characteristic determination unit 44 determines a tissue characteristic in the area of interest of the sample on the basis of the feature data extracted by the feature data extractor 43 and corrected by the attenuation corrector 432 and the known sample information stored in the known sample information storage unit 81 (Step S11).

Here, the process (Step S11) which is performed by the tissue characteristic determination unit 44 will be described in detail with reference to the flowchart shown in FIG. 11. First, the tissue characteristic determination unit 44 sets a feature data space to be used in determining the tissue characteristic (Step S41). In the first embodiment, two of the three pieces of feature data, that is, a gradient a, an intercept b, and a strength c, are independent parameters. Accordingly, a two-dimensional space with optional two of the three pieces of feature data as components can be set as a feature data space. In addition, a one-dimensional space with optional one of the three pieces of feature data as a component can also be set as the feature data space. In Step S41, although the feature data space to be set is determined in advance, the operator may select a desired feature data space through the input unit 6.

FIG. 12 is a diagram illustrating an example of the feature data space set by the tissue characteristic determination unit 44. In the feature data space shown in FIG. 12, the horizontal axis represents the intercept b, and the vertical axis represents the strength c. The point Sp shown in FIG. 12 represents a point having the intercept b and the strength c as coordinates of the feature data space, which have been calculated with respect to a sample as a determination target (hereinafter, this point is referred to as "sample point"). In addition, the areas $G_\mu$, $G_\nu$, and $G_\rho$ shown in FIG. 12 represent groups in which the tissue characteristics of known samples stored in the known sample information storage unit 81 are μ, ν, and ρ, respectively. In the case shown in FIG. 12, each of the three groups $G_\mu$, $G_\nu$, and $G_\rho$ is present in an area which does not intersect with other groups on the feature data space.

In the first embodiment, even when obtaining the feature data of known samples, tissue characteristics are classified and determined using the feature data as an index, obtained by subjecting the pre-correction feature data of the frequency spectrum obtained by frequency analysis to attenuation correction. Accordingly, the tissue characteristics different from each other can be sharply distinguished. Particularly, in the first embodiment, since feature data subjected to attenuation correction is used, the areas of the respective tissue characteristics in the feature data space can be separated more clearly than in the case in which feature data extracted without performing attenuation correction is used.

After Step S41, the tissue characteristic determination unit 44 calculates distances $d_\mu$, $d_\nu$, and $d_\rho$ on the feature data space between the sample point Sp and points $\mu_0$, $\nu_0$, and $\rho_0$ (hereinafter, these points are referred to as "known sample average points") which have, as coordinates in the feature data space, an average of the intercept b and an average of the strength c of the frequency spectrum of the FFT data group included in the groups $G_\mu$, $G_\nu$, and $G_\rho$ respectively (Step S42). Here, when the scales of the b-axis component and the c-axis component in the feature data space are significantly different from each other, it is desirable to appropriately perform weighting for approximately equalizing the contribution of each distance.

Next, the tissue characteristic determination unit 44 determines tissue characteristics of all of sample points including the sample point Sp on the basis of the distances calculated in Step S42 (Step S43). For example, in the case shown in FIG. 12, the distance $d_\mu$ is the minimum, and thus the tissue characteristic determination unit 44 determines that the tissue characteristic of the sample is μ. When the sample point Sp is extremely distant from the known sample average points $\mu_0$, $\nu_0$, and $\rho_0$, the result of the tissue characteristic determination has low reliability even when minimum values of the distances $d_\mu$, $d_\nu$, and $d_\rho$ are obtained. Therefore, when $d_\rho$, $d_\nu$, and $d_\rho$ are greater than a predetermined threshold, the tissue characteristic determination unit 44 may output an error signal. In addition, when values of two or more of $d_\mu$, $d_\nu$, and $d_\rho$ are minimum, the tissue characteristic determination unit 44 may select all of the tissue characteristics corresponding to the minimum values as candidates, or may select any one tissue characteristic in accordance with a predetermined rule. Examples of the latter case include a method in which the priority of a highly malignant tissue characteristic such as cancer is set to be high. In addition, when values of two or more of $d_\mu$, $d_\nu$, and $d_\rho$ are minimum, the tissue characteristic determination unit 44 may output an error signal.

Then, the tissue characteristic determination unit 44 outputs the distance calculation result in Step S42 and the determination result in Step S43 (Step S44). Accordingly, the tissue characteristic determination process in Step S11 is terminated.

After the above-described Step S11, the feature data image data generator 52 generates feature data image data to display visual information corresponding to the feature data extracted by the feature data extractor 43 (Step S12).

Next, the determination result display image data generator 53 generates determination result display image data using the B-mode image data generated by the B-mode image data generator 51, the feature data calculated by the feature data extractor 43, the feature data image data generated by the feature data image data generator 52, and the determination result obtained by the tissue characteristic determination unit 44 (Step S13).

Figure 13:
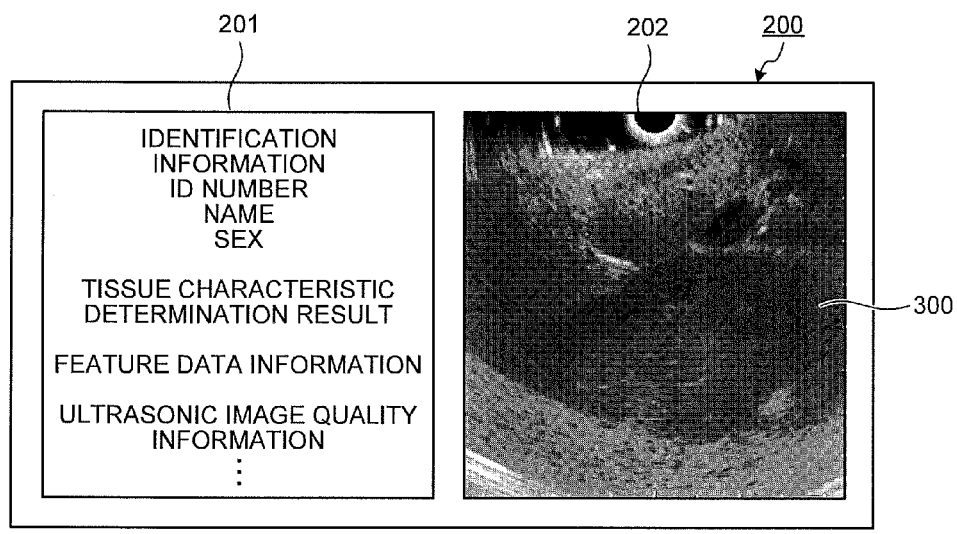
FIG. 13 is a diagram illustrating a display example of a determination result display image which is displayed by the display unit of the ultrasonic observation apparatus according to the first embodiment of the invention.

Then, the display unit 7 displays the determination result display image generated by the determination result display image data generator 53 (Step S14). FIG. 13 is a diagram illustrating a display example of the determination result display image which is displayed by the display unit 7. A determination result display image 200 shown in FIG. 13 has an information display unit 201 which displays various related information including the result of the tissue characteristic determination and an image display unit 202 which displays a feature data image to display the feature data on the basis of the B-mode image.

The information display unit 201 displays identification information (ID number, name, sex, and the like) of a sample, the tissue characteristic determination result calculated by the tissue characteristic determination unit 44, information related to the feature data in determining the tissue characteristic, and ultrasonic image quality information such as gain and contrast. Here, as the information related to the feature data, it is possible to perform a display using averages and standard deviations of the feature data of the frequency spectrums of FFT data of Q groups positioned inside the area of interest. Specifically, the information display unit 201 can display, for example, gradient=1.5±0.3 (dB/MHz), intercept=−60±2 (dB), and strength=−50±1.5 (dB).

A feature data image 300 which is displayed on the image display unit 202 is a gray scale image in which regarding the B-mode image 100 shown in FIG. 5, the intercept b is uniformly assigned to R (red), G (green), and B (blue).

When the display unit 7 displays the determination result display image 200 having the above-described configuration, the operator can more accurately grasp the tissue characteristic of the area of interest. The determination result display image is not limited to the above-described configuration. For example, the feature data image and the B-mode image may be displayed next to each other as the determination result display image. Accordingly, the difference between both of the images can be recognized on the one screen.

Figure 14:
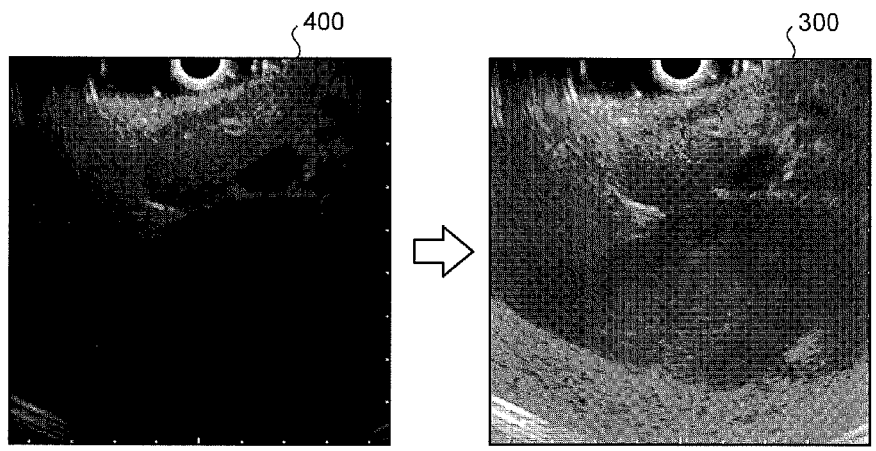
FIG. 14 is a diagram explaining an effect of an attenuation correction process which is performed by the ultrasonic observation apparatus according to the first embodiment of the invention.

FIG. 14 is a diagram explaining an effect of the attenuation correction process which is performed by the ultrasonic observation apparatus 1. An image 400 shown in FIG. 14 is a feature data image when attenuation correction is not performed. In the case of the feature data image 400, the signal strength is reduced due to the influence of attenuation in an area with a high receiving depth (lower area in FIG. 14), whereby the image becomes dark. On the contrary, it is found that in the feature data image 300 subjected to the attenuation correction, an image having uniform brightness is obtained over the entire screen.

The feature data images 300 shown in FIGS. 13 and 14 are just an example. For example, three feature data items a', b', and c' can be assigned to R, G, and B, respectively, to display a feature data image by a color image. In this case, since the tissue characteristic is expressed with a unique color, the operator can grasp the tissue characteristic of the area of interest on the basis of the color distribution of the image. In addition, the color space may be formed of, in place of the RGB color system, variables which are complementary colors such as cyan, magenta, and yellow, and feature data may be assigned to the respective variables. In addition, the B-mode image data and the color image data may be mixed at a predetermined ratio to generate the feature data image data. In addition, only the area of interest may be substituted with color image data to generate the feature data image data.

According to the above-described the first embodiment of the invention, B-mode image data is generated on the basis of a signal which is subjected to STC correction for amplification with an amplification factor according to the receiving depth. In addition, pre-correction feature data is extracted by performing amplification correction for offsetting the influence of the STC correction and for thereby making the amplification factor spectrum-constant, and by then calculating the frequency spectrum, feature data of a sample is extracted by subjecting the extracted pre-correction feature data to attenuation correction, and feature data image data is generated to display visual information corresponding to the extracted feature data. Accordingly, the influence of the attenuation accompanying the transmission of an ultrasonic wave is eliminated in the feature data image data, and it is not necessary to separately send a signal for a B-mode image and a signal for a feature data image. Accordingly, it is possible to properly eliminate the influence of the attenuation accompanying the transmission of an ultrasonic wave, and also possible to prevent a reduction in the frame rate of image data generated on the basis of the received ultrasonic wave.

In addition, according to the first embodiment, since the tissue characteristic of a predetermined area of a sample is determined by using the feature data of the frequency spectrum properly subjected to attenuation correction, the difference between tissues can be sharply distinguished without using the distortion amount or elastic modulus of a living tissue. Accordingly, the tissue characteristic can be accurately distinguished and the reliability of the observation result can be improved.

As a modified example of the first embodiment, the controller 9 may allow the amplification correction process using the amplification corrector 41 and the attenuation correction process using the attenuation corrector 432 to be collectively performed. For this process, the amplification process in Step S6 of FIG. 4 is deleted and the definition of the attenuation amount of the attenuation correction process in Step S10 of FIG. 4 is changed as in the following Expression (6):

$$A' = 2\alpha z f + \gamma(z) \quad (6)$$

Here, $\gamma(z)$ on the right side is a difference between the amplification factors $\beta$ and $\beta_0$ at the receiving depth z, and is represented as follows:

$$\gamma(z) = -\{(\beta_{th} - \beta_0)/z_{th}\}z + \beta_{th} - \beta_0 \ (z \leq z_{th}) \quad (7)$$

$$\gamma(z) = 0 \ (z > z_{th}) \quad (8)$$

Second Embodiment

A second embodiment of the invention is different from the first embodiment in terms of the feature data extraction which is performed by the feature data extractor. The configuration of an ultrasonic observation apparatus according to the second embodiment is the same as that of the ultrasonic observation apparatus 1 described in the first embodiment. Accordingly, in the following description, constituent elements corresponding to the constituent elements of the ultrasonic observation apparatus 1 will be denoted by the same signs.

In the feature data extraction process in the second embodiment, first, an attenuation corrector 432 subjects a frequency spectrum calculated by a frequency analyzer 42 to an attenuation correction process. Then, an approximation unit 431 subjects the frequency spectrum subjected to the attenuation correction using the attenuation corrector 432 to an approximation process to extract feature data of the frequency spectrum.

Figure 15:
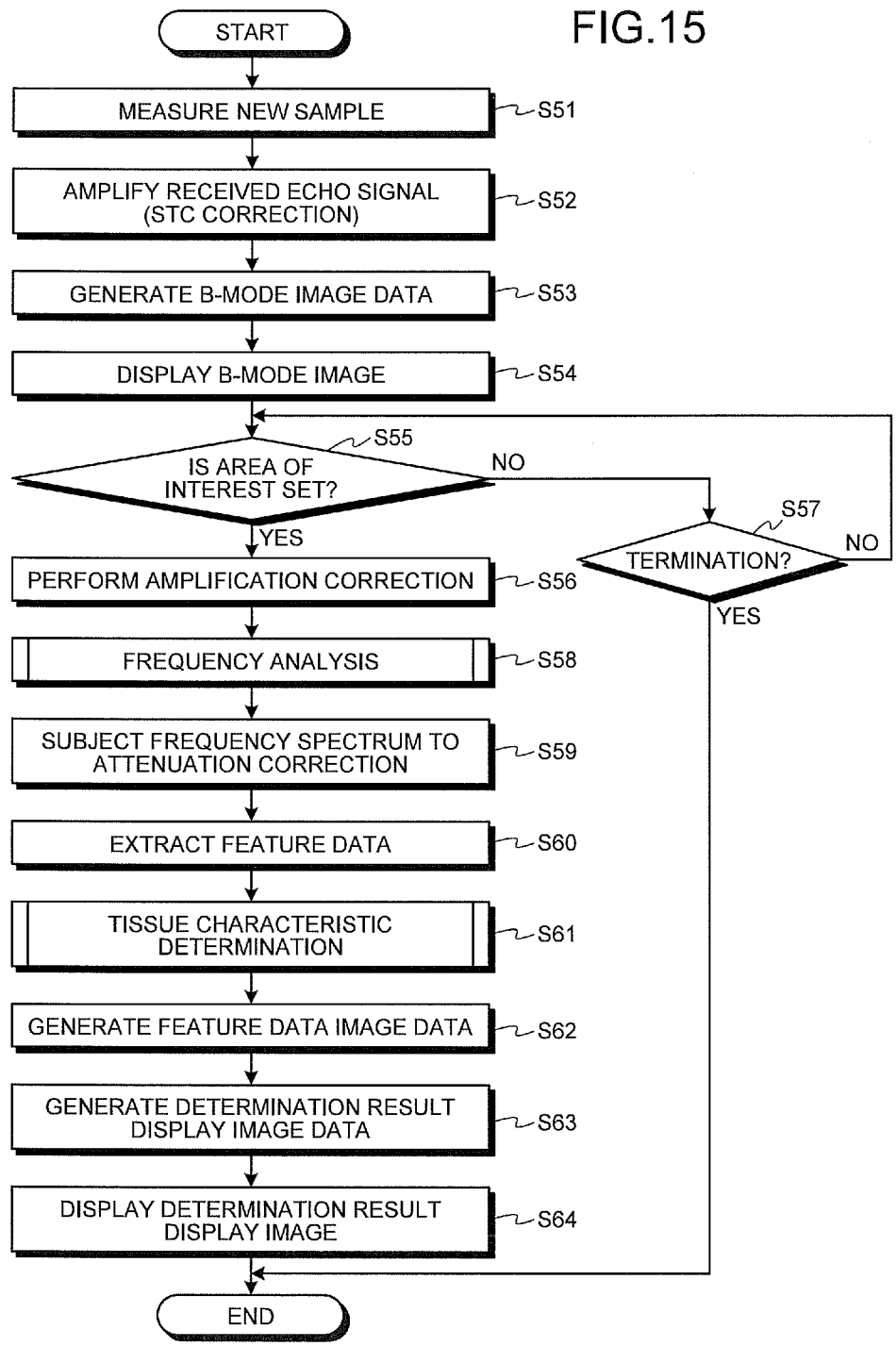
FIG. 15 is a flowchart illustrating the outline of a process which is performed by an ultrasonic observation apparatus according to a second embodiment of the invention.

FIG. 15 is a flowchart illustrating the outline of a process of the ultrasonic observation apparatus according to the second embodiment. In FIG. 15, processes in Steps S51 to S58 sequentially correspond to the processes in Steps S1 to S8 of FIG. 4.

Figure 16:
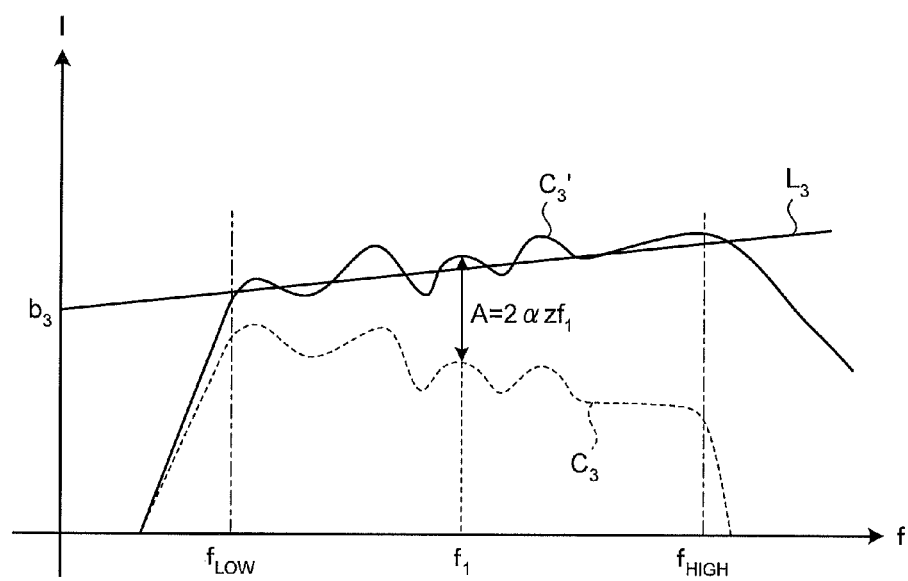
FIG. 16 is a diagram schematically illustrating the outline of an attenuation correction process which is performed by the ultrasonic observation apparatus according to the second embodiment of the invention.

In Step S59, the attenuation corrector 432 subjects the frequency spectrum calculated by the frequency analyzer 42 through FFT computing to attenuation correction (Step S59). FIG. 16 is a diagram schematically illustrating the outline of the attenuation correction process in Step S59. As shown in FIG. 16, the attenuation corrector 432 corrects a frequency spectrum curve $C_3$ at all of frequencies f so that the attenuation amount A of the above-described Expression (1) is added to a strength I, thereby obtaining a new frequency spectrum curve $C_3'$. Accordingly, a frequency spectrum can be obtained in which the contribution of attenuation accompanying the transmission of an ultrasonic wave is reduced.

Then, the approximation unit 431 subjects all of the frequency spectrums subjected to the attenuation correction using the attenuation corrector 432 to regression analysis to extract feature data of the frequency spectrum (Step S60). Specifically, the approximation unit 431 performs regression analysis, thereby calculating a gradient a and an intercept b of a linear expression and a strength c at a center frequency $f_{MID}$. A straight line $L_3$ shown in FIG. 16 is a regression line (intercept $b_3$) which is obtained by subjecting the frequency spectrum curve $C_3$ to a feature data extraction process in Step S60.

Processes in Steps S61 to S64 sequentially correspond to the processes in Steps S11 to S14 of FIG. 4.

According to the above-described the second embodiment of the invention, B-mode image data is generated on the basis of a signal which is subjected to STC correction for amplification with an amplification factor according to the receiving depth. In addition, amplification correction for offsetting the influence of the STC correction and for thereby making the amplification factor spectrum-constant is performed, a frequency spectrum is calculated and subjected to attenuation correction, and then feature data is extracted and feature data image data is generated to display visual information corresponding to the extracted feature data. Accordingly, the influence of the attenuation accompanying the transmission of an ultrasonic wave is eliminated in the feature data image data, and it is not necessary to separately send a signal for a B-mode image and a signal for a feature data image. Accordingly, as in the above-described the first embodiment, it is possible to properly eliminate the influence of the attenuation accompanying the transmission of an ultrasonic wave, and also possible to prevent a reduction in the frame rate of image data generated on the basis of the received ultrasonic waves.

In addition, according to the second embodiment, since the tissue characteristic of a predetermined area of a sample is determined by using the feature data of the frequency spectrum properly subjected to attenuation correction, the difference between tissues can be sharply distinguished without using the distortion amount or elastic modulus of a living tissue. Accordingly, the tissue characteristic can be accurately distinguished and the reliability of the observation result can be improved.

Also, in the second embodiment, the amplification correction process in Step S56 of FIG. 15 can be deleted and the attenuation amount in performing the attenuation correction of the frequency spectrum in Step S59 of FIG. 15 can be processed as A' of Expression (6).

Third Embodiment

A third embodiment of the invention is different from the first embodiment in terms of the tissue characteristic determination process in the tissue characteristic determination unit. The configuration of an ultrasonic observation apparatus according to the third embodiment is the same as that of the ultrasonic observation apparatus 1 described in the first embodiment. Accordingly, in the following description, constituent elements corresponding to the constituent elements of the ultrasonic observation apparatus 1 will be denoted by the same signs.

A tissue characteristic determination unit 44 adds feature data (a, b, c) to groups $G_\mu$, $G_\nu$, and $G_\rho$ (see FIG. 12) which constitute tissue characteristics μ, ν, and ρ, respectively, to constitute a new population, and then obtains a standard deviation for each feature data of data constituting each tissue characteristic.

Then, the tissue characteristic determination unit 44 calculates a difference (hereinafter, simply referred to as "standard deviation difference") between the standard deviation of each feature data of the groups $G_\mu$, $G_\nu$, and $G_\rho$ in the original population formed of known samples and the standard deviation of each feature data of the groups $G_\mu$, $G_\nu$, and $G_\rho$ in the new population having new samples added thereto, and determines the tissue characteristic corresponding to the group including the feature data which is minimum in the standard deviation difference as a tissue characteristic of the sample.

Here, the tissue characteristic determination unit 44 may calculate the standard deviation difference only with respect to the standard deviation of feature data selected in advance from a plurality of pieces of feature data. In this case, the feature data may be arbitrarily selected by an operator, or may be automatically selected by the ultrasonic observation apparatus 1.

In addition, the tissue characteristic determination unit 44 may calculate a value for each group, by performing appropriate weighting to the standard deviation differences of all pieces of feature data and adding the weighted values, and may determine the tissue characteristic corresponding to the group which is minimum in terms of the value as a tissue characteristic of the sample. In this case, for example, when the feature data includes a gradient a, an intercept b, and a strength c, the tissue characteristic determination unit 44 calculates $w_a$·(standard deviation difference of a)+$w_b$·(standard deviation difference of b)+$w_c$·(standard deviation difference of c) (where $w_a$, $w_b$, and $w_c$ are weights corresponding to the gradient a, the intercept b, and the strength c, respectively), and determines the tissue characteristic of the sample on the basis of the calculated value. The values of the weights $w_a$, $w_b$, and $w_c$ may be arbitrarily set by an operator, or may be automatically set by the ultrasonic observation apparatus 1.

In addition, the tissue characteristic determination unit 44 may calculate a square root of a value which is calculated for each group by performing appropriate weighting to the squares of the standard deviation differences of all pieces of feature data and adding the weighted values, and may determine the tissue characteristic corresponding to the group which is minimum in terms of the square root as a tissue characteristic of the sample. In this case, for example, when the feature data includes a gradient a, an intercept b, and a strength c, the tissue characteristic determination unit 44 calculates ($w'_a$·(standard deviation difference of a)$^2$+$w'_b$·(standard deviation difference of b)$^2$+$w'_c$·(standard deviation difference of c)$^2$)$^{1/2}$ (where $w'_a$, $w'_b$, and $w'_c$ are weights corresponding to the gradient a, the intercept b, and the strength c, respectively), and determines the tissue characteristic on the basis of the calculated value. Also, in this case, the values of the weights $w'_a$, $w'_b$, and $w'_c$ may be arbitrarily set by an operator, or may be automatically set by the ultrasonic observation apparatus 1.

According to the above-described the third embodiment of the invention, as in the above-described the first embodiment, it is possible to properly eliminate the influence of the attenuation accompanying the transmission of an ultrasonic wave, and also possible to prevent a reduction in the frame rate of image data generated on the basis of the received ultrasonic wave.

In addition, according to the third embodiment, the tissue characteristic can be accurately distinguished, and the reliability of the observation result can be improved. In addition, the influence of the attenuation accompanying the transmission of an ultrasonic wave is eliminated and thus the tissue characteristic can be determined with higher accuracy.

In the third embodiment, although the tissue characteristic determination unit 44 determines the tissue characteristic on the basis of a change in the standard deviations of the respective pieces of feature data between the original population and the population having new samples added thereto, this is just an example. For example, the tissue characteristic determination unit 44 may determine the tissue characteristic on the basis of a change in the averages of the respective pieces of feature data between the original population and the population having new samples added thereto.

Although the embodiments of the invention have been described as above, the invention is not limited only to the above-described first to third embodiments. That is, the invention can be implemented in various forms without departing from the technical idea described in the claims.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic observation apparatus comprising:
   an ultrasonic probe configured to output an ultrasonic wave to a sample and to receive the ultrasonic wave reflected from the sample; and
   at least one processor comprising hardware, the at least one processor being configured to execute:
      a signal amplification operation for amplifying a signal of the ultrasonic wave reflected from the sample with an amplification factor according to a receiving depth and to perform sensitivity time control (STC) correction;
      a B-mode image data generation operation for generating B-mode image data from the signal of the ultrasonic wave, the B-mode image data having an amplitude amplified by the signal amplification operation being converted into brightness for display;
      an amplification correction operation for performing amplification correction to offset an influence of the STC correction according to the receiving depth by the signal amplification operation in order to make the amplification factor constant with respect to the signal of the ultrasonic wave amplified by the signal amplification operation regardless of the receiving depth;
      a frequency analyzing operation for calculating a frequency spectrum by analyzing the frequency of the signal of the ultrasonic wave corrected by the amplification correction operation; and
      a feature data extraction operation for extracting feature data of the sample by performing an approximation process and an attenuation correction process for reducing the contribution of the attenuation occurring in accordance with the receiving depth of the ultrasonic wave and the frequency in transmitting the ultrasonic wave,
   wherein the feature data extraction operation comprises:
      an approximation operation for approximating the frequency spectrum calculated by the frequency analyzing operation with a linear expression through regression analysis and to calculate pre-correction feature data including a gradient $a_0$ and an intercept $b_0$ of the linear expression; and
      an attenuation correction operation for performing an attenuation correction with respect to the pre-correction feature data calculated by the approximation operation in accordance with a gradient a and an intercept b of the approximated linear expression expressed by:

$a = a_0 + 2\alpha z$, and $b = b_0$, where $\alpha$ represents an attenuation rate, and z represents a reception depth of ultrasonic waves.

2. The ultrasonic observation apparatus according to claim 1, wherein the amplification factor in performing the amplification using the signal amplification operation monotonically increases at a receiving depth of up to a predetermined receiving depth.

3. The ultrasonic observation apparatus according to claim 1,
   wherein the feature data extraction operation comprises:
      an approximation operation for extracting pre-correction feature data before performing the attenuation correction operation by subjecting the frequency spectrum calculated by the frequency analyzing operation to the approximation operation; and
      an attenuation correction operation for extracting feature data of the frequency spectrum by subjecting the pre-correction feature data extracted by the approximation operation to the attenuation correction operation, and
   wherein the greater the receiving depth of the ultrasonic wave, the greater the correction amount the attenuation correction operation performs correction with.

4. The ultrasonic observation apparatus according to claim 1,
   wherein the feature data extraction operation comprises:
      an approximation operation for extracting pre-correction feature data before performing the attenuation correction operation by subjecting the frequency spectrum calculated by the frequency analyzing operation to the approximation operation; and
      an attenuation operation for extracting feature data of the frequency spectrum by subjecting the pre-correction feature data extracted by the approximation operation to the attenuation correction operation, and
   wherein the ultrasonic observation apparatus further comprises a controller configured to allow the correction of the amplification correction operation and the correction of the attenuation correction operation to be collectively performed.

5. The ultrasonic observation apparatus according to claim 1, further comprising a memory configured to store the feature data of the frequency spectrum extracted on the basis of ultrasonic waves reflected by a plurality of known samples in association with tissue characteristics of the plurality of known samples, and
   wherein the at least one processor further implements a tissue characteristic determination operation for determining a tissue characteristic of a predetermined area of the sample by using the feature data stored in association with the plurality of known samples in the memory and the feature data extracted by the feature data extraction operation.

6. The ultrasonic observation apparatus according to claim 1, wherein the at least one processor further implements a feature data image data generation operation for generating feature data image data to display visual information corresponding to the feature data extracted by the feature data extraction operation.

7. The ultrasonic observation apparatus according to claim 6, wherein the visual information is a variable constituting a color space.

8. The ultrasonic observation apparatus according to claim 1,
wherein the feature data extraction operation comprises:
an approximation operation for extracting pre-correction feature data before performing the attenuation correction operation by subjecting the frequency spectrum calculated by the frequency analyzing operation to the approximation operation; and
an attenuation correction operation for extracting feature data of the frequency spectrum by subjecting the pre-correction feature data extracted by the approximation operation to the attenuation correction process, and
wherein the attenuation correction process is performed using a predetermined attenuation rate which is determined in accordance with the sample.

9. The ultrasonic observation apparatus according to claim 8, further comprising an input device configured to receive an input of information that changes the attenuation rate.

10. A method of operating an ultrasonic observation apparatus for sending an ultrasonic wave to a sample and receiving the ultrasonic wave reflected by the sample, the method comprising:
amplifying a signal of the ultrasonic wave reflected from the sample with an amplification factor according to a receiving depth and performing sensitivity time control (STC) correction;
generating B-mode image data from the signal of the ultrasonic wave, and converting the B-mode image data having an amplitude amplified by the amplifying into brightness for display using a B-mode image data generator;
performing amplification correction to offset an influence of the STC correction according to the receiving depth by the amplifying in order to make the amplification factor constant with respect to the amplified signal of the ultrasonic wave regardless of the receiving depth;
calculating a frequency spectrum using a frequency analyzing operation by analyzing the frequency of the corrected signal of the ultrasonic wave; and
extracting feature data of the sample using a feature data extractor by performing an approximation process and an attenuation correction process for reducing the contribution of the attenuation occurring in accordance with the receiving depth of the ultrasonic wave and the frequency in transmitting the ultrasonic wave,
wherein the step of extracting feature data comprises:
approximating the frequency spectrum calculated by the frequency analyzing operation with a linear expression through regression analysis and to calculate pre-correction feature data including a gradient $a_0$ and an intercept $b_0$ of the linear expression; and
performing an attenuation correction with respect to the pre-correction feature data calculated by the step of approximating the frequency spectrum in accordance with a gradient a and an intercept b of the approximated linear expression expressed by:

$a = a_0 + 2\alpha z$, and $b = b_0$, where $\alpha$ represents an attenuation rate, and z represents a reception depth of ultrasonic waves.

11. A non-transitory computer readable recording medium on which an executable program is recorded, the program instructing a processor to execute:
amplifying a signal of the ultrasonic wave reflected from the sample with an amplification factor according to a receiving depth and performing sensitivity time control (STC) correction;
generating B-mode image data from the signal of the ultrasonic wave, and converting the B-mode image data having an amplitude by the amplifying into brightness for display using a B-mode image data generator;
performing amplification correction to offset an influence of the STC correction according to the receiving depth in order to make the amplification factor constant with respect to the amplified signal of the ultrasonic wave regardless of the receiving depth; and
calculating a frequency spectrum using a frequency analyzing operation by analyzing the frequency of the corrected signal of the ultrasonic wave, and extracting feature data of the sample using a feature data extractor by performing an approximation process and an attenuation correction process for reducing the contribution of the attenuation occurring in accordance with the receiving depth of the ultrasonic wave and the frequency in transmitting the ultrasonic wave,
wherein the step of extracting feature data comprises:
approximating the frequency spectrum calculated by the frequency analyzing operation with a linear expression through regression analysis and to calculate pre-correction feature data including a gradient $a_0$ and an intercept $b_0$ of the linear expression; and
performing an attenuation correction with respect to the pre-correction feature data calculated by the step of approximating the frequency spectrum in accordance with a gradient a and an intercept b of the approximated linear expression expressed by:

$a = a_0 + 2\alpha z$, and $b = b_0$, where $\alpha$ represents an attenuation rate, and z represents a reception depth of ultrasonic waves.

* * * * *